US00PP32028P3

(12) United States Plant Patent
Lyrene et al.

(10) Patent No.: US PP32,028 P3
(45) Date of Patent: Aug. 4, 2020

(54) BLUEBERRY PLANT NAMED 'OPTIMUS'

(50) Latin Name: ***Vaccinium corymbosum* L.**
Varietal Denomination: OPTIMUS

(71) Applicant: Florida Foundation Seed Producers, Inc., Marianna, FL (US)

(72) Inventors: Paul M. Lyrene, Micanopy, FL (US); James W. Olmstead, Watsonville, CA (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/350,892

(22) Filed: Jan. 29, 2019

(65) Prior Publication Data

US 2019/0281738 P1 Sep. 12, 2019

Related U.S. Application Data

(60) Provisional application No. 62/640,517, filed on Mar. 8, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

U.S. PATENT DOCUMENTS

| | | | |
|---|---|---|---|
| PP10,675 | P | 11/1998 | Lyrene |
| PP12,165 | P2 | 10/2001 | Lyrene |
| PP16,404 | P3 | 4/2006 | Lyrene |
| PP26,312 | P2 | 1/2016 | Lyrene et al. |
| PP26,313 | P2 | 1/2016 | Lyrene et al. |
| PP26,523 | P3 | 3/2016 | Lyrene |
| PP26,679 | P2 | 5/2016 | Lyrene et al. |
| PP27,325 | P3 | 11/2016 | Lyrene |
| PP27,576 | P3 | 1/2017 | Lyrene |
| PP27,740 | P2 | 3/2017 | Norden et al. |
| PP27,771 | P2 | 3/2017 | Lyrene et al. |

OTHER PUBLICATIONS

U.S. Appl. No. 16/350,811, filed Jan. 15, 2019, Lyrene.
U.S. Appl. No. 16/350,891, filed Jan. 29, 2019, Lyrene.

*Primary Examiner* — Susan McCormick Ewoldt
(74) *Attorney, Agent, or Firm* — Dentons US LLP

(57) ABSTRACT

'OPTIMUS' is a new and distinct southern highbush blueberry (*Vaccinium corymbosum* L.) variety distinguished at least by a low chilling requirement, particularly for the flower buds; good field disease resistance; vigorous, upright growth habit; earlier fruit ripening; and round, firm, sweet fruit that are medium in size, suitable for machine harvest, and have very small, dry picking scars.

3 Drawing Sheets

Latin name of the genus and species of the plant claimed: *Vaccinium corymbosum* L.

Variety denomination: 'OPTIMUS'.

BACKGROUND OF THE INVENTION

The present invention relates to a new and distinct hybrid variety of southern highbush blueberry (*Vaccinium corymbosum* L.) named 'OPTIMUS'. 'OPTIMUS' is a blueberry clone that can be distinguished at least by its low chilling requirement, particularly for the flower buds; good field disease resistance; and vigorous, upright growth habit. 'OPTIMUS' can also be distinguished at least by its fruit that are round, firm, sweet, medium in size, suitable for machine harvest, and have very small, dry picking scars. When grown in North-central Florida, 90% of the fruit are normally harvested between April 5 and May 5. 'OPTIMUS' has been asexually propagated by softwood stem cuttings in Gainesville and Waldo, Fla., and the resulting plants have all been phenotypically indistinguishable from the original plant.

'OPTIMUS' originated as a seedling from a cross between 'FL96-22' (unpatented) as the female (seed) parent and 'Cor00-17' (unpatented) as the male (pollen) parent.

This cross was made in Gainesville, Fla. in February, 2005. The seedling was planted in a high-density field nursery in May, 2006, and the first fruit were evaluated in April, 2007. 'OPTIMUS' was first asexually propagated in Gainesville, Fla. by softwood stem cuttings in 2008. After the second year of fruiting in the field, in the spring of 2008, 'OPTIMUS' was propagated by softwood stem cuttings, and an experimental 15-plant test plot was established as part of a variety test at Windsor, Fla., in January, 2009. At this time, the experimental code 'FL08-262' was assigned to 'OPTIMUS'. Based on the growth, yield, and fruit quality of this plot, 'OPTIMUS' was propagated by softwood stem cuttings and additional experimental test plots ranging from 5 to 45 plants were established in experimental research trials across Florida. These plots have been observed during flowering and ripening each year, and no mutations or off-type plants have been observed.

'EMERALD', (U.S. Plant Pat. No. 12,165) is an important southern highbush blueberry variety that is planted throughout the southeastern United States. 'OPTIMUS' displays a more upright and vigorous growth habit and produces earlier, machine harvestable fruit than 'Emerald'.

'OPTIMUS' also has higher early fruit yield than both 'FL96-22', its female parent, and 'Cor00-17', its male parent.

SUMMARY OF THE INVENTION

The following are characteristics of 'OPTIMUS' when grown under normal horticultural practices in Florida. 'OPTIMUS' exhibits a low chilling requirement, particularly for the flower buds; good field disease resistance; vigorous, upright growth habit; earlier fruit ripening; and round, firm, sweet fruit that are medium in size and have very small, dry picking scars. 'OPTIMUS' was also selected specifically for machine harvest characteristics.

BRIEF DESCRIPTION OF THE DRAWINGS

The accompanying photographs show typical bush, flower, and fruit characteristics for 'OPTIMUS'. Colors shown are as true as can be reasonably reproduced by photographic procedures and may differ from those cited in the detailed description, which accurately describes the colors of 'OPTIMUS'.

DETAILED BOTANICAL DESCRIPTION

Figure 1:
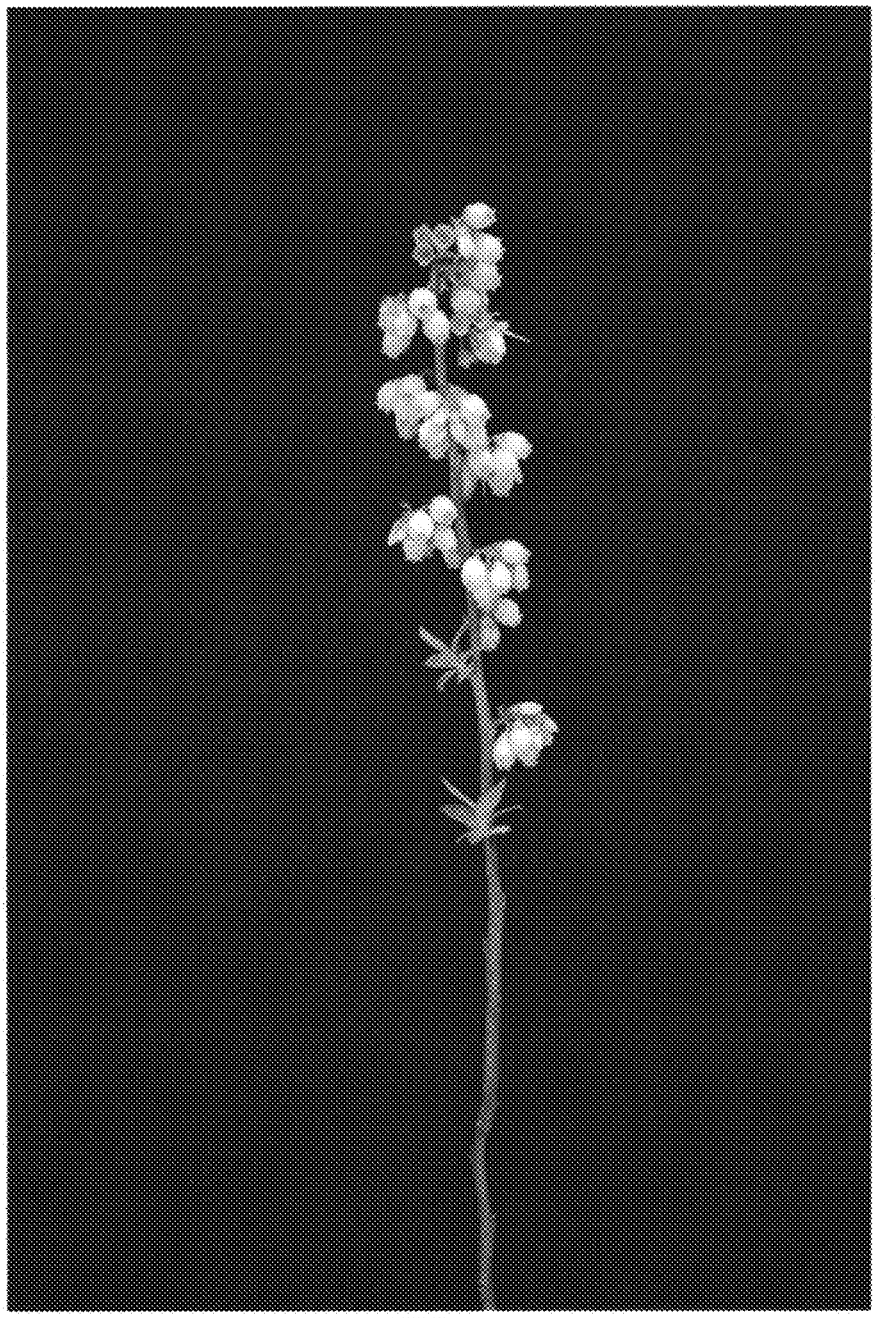
FIG. 1—Shows several clusters of opening 'OPTIMUS' flowers.
Figure 2:
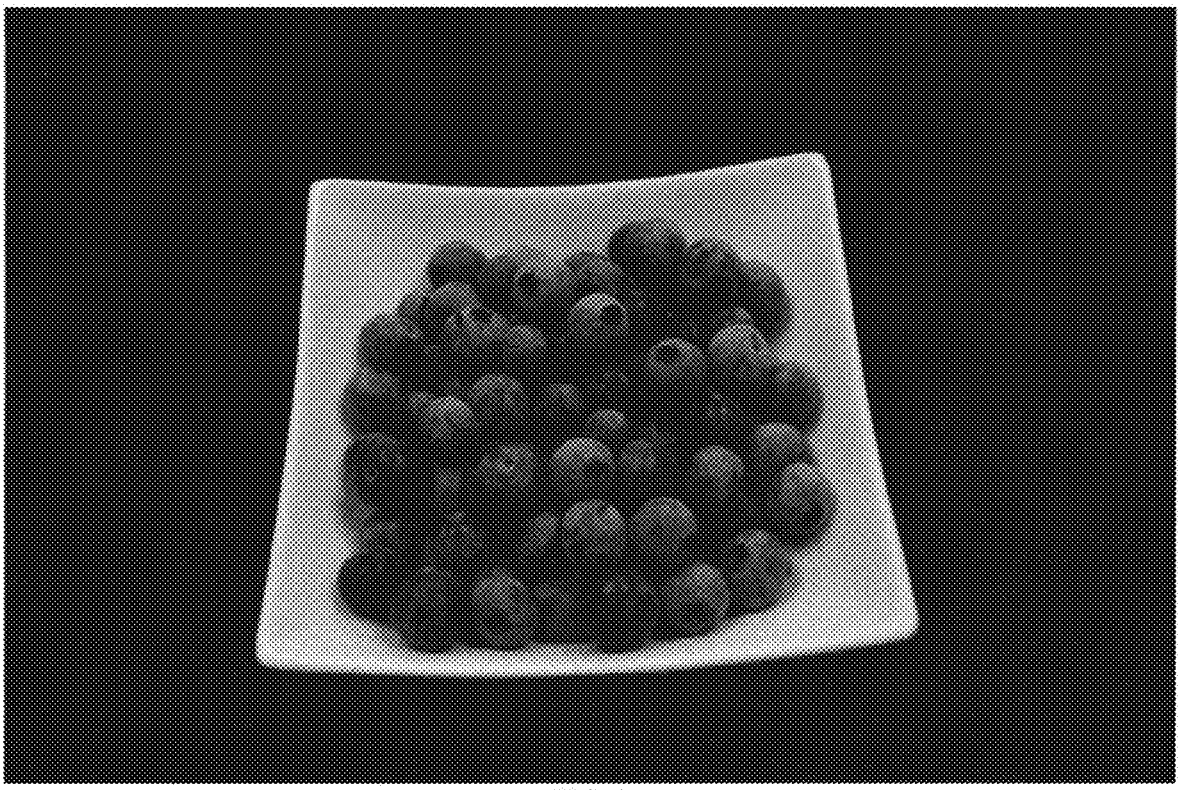
FIG. 2—Shows a close-up of harvested 'OPTIMUS' berries.
Figure 3:
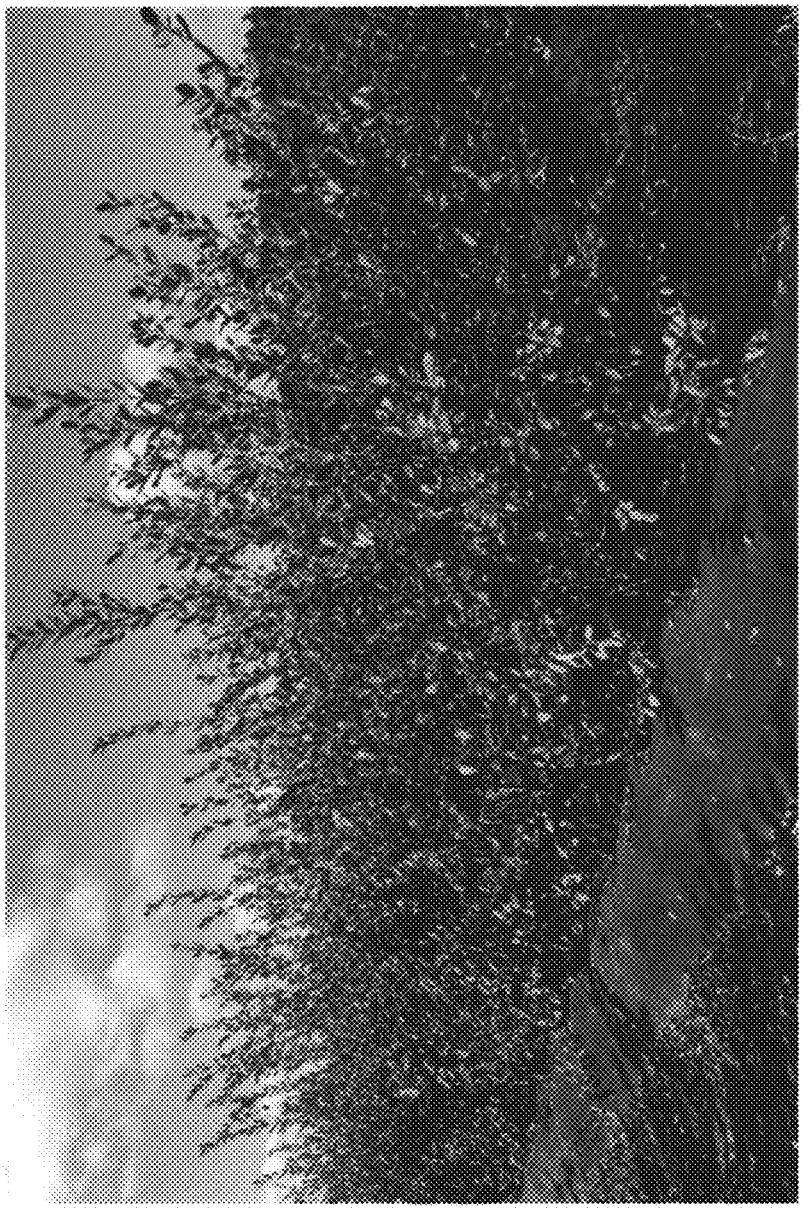
FIG. 3—Shows several five-year-old 'OPTIMUS' plants in November with the vigorous, semi-upright plant architecture visible.

The following detailed description sets forth distinctive characteristics of 'OPTIMUS'. The data that define these characteristics were collected from asexual reproductions carried out in Florida. The plant history was taken on a plot of plants growing in an experimental trial near Windsor, Fla. The plant was 5 years of age when the data was collected. Certain characteristics may vary with plant age. 'OPTIMUS' has not been observed under all possible environmental conditions, and the measurements given may vary when grown in different environments. Color descriptions are based on The Royal Horticultural Society (R.H.S.) Colour Chart by the Royal Horticultural Society, London, Fifth Edition, 2007. If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'OPTIMUS'.

Plant:

*Plant vigor*.—High.

*Growth habit*.—Semi-upright.

*Plant height*.—1.91 m on average for 5-year old plant.

*Plant spread*.—1.74 m on average for 5-year old plant.

*Flower bud density* (*number*) *along flowering twigs in January*.—High.

*Twigginess*.—Medium-high.

*Tendency toward evergreenness*.—Medium-Low

*Productivity*.—In northeast Florida, 'OPTIMUS' produces 4-5 kg per season from plants 5 years old or older when hand harvested.

*Chilling requirement*.—200 hours below 7° C.

*Cold hardiness*.—'OPTIMUS' has been grown in temperate climates with extremely cold winter temperatures. Plants have survived winter freezes of −7° C. with minimal damage.

*Ease of propagation*.—'OPTIMUS' has only been propagated from softwood stem cuttings, where the rooting percentage is greater than 85% and comparable to other varieties.

Trunk and branches:

*Suckering tendency*.—Low.

*Surface texture* (*of strong, 12-month-old shoots observed in October*).—Moderate Smooth (little to no presence of ridges and bark-like structure).

*Surface texture* (*of 3-year-old and older wood*).—Very Smooth.

*Color of new twigs observed in the field*.—Fan 3 145B yellow-green group.

*Color of 3-year-old, rough-textured canes*.—Fan 4 199C grey brown group.

*Internode length* (*strong, upright shoots measured in June*).—Mean of 17.8 mm.

Leaves:

*Leaf arrangement*.—Alternate, Fibonacci Spiral.

*Length* (*including petiole, from tip of petiole to end of blade*).—Mean of 5.840 cm.

*Width* (*at widest point*).—Mean of 3.028 cm.

*Petiole length*.—Mean of 3.54 mm.

*Petiole diameter*.—Mean of 1.71 mm.

*Leaf shape*.—Elliptic, with the leaf apex having a small point.

*Leaf base shape*.—Elliptic.

*Leaf venation pattern*.—Cross-venulate.

*Margin*.—Entire.

*Color*.—Upper surface: Fan 3 green group 139A. Lower surface: Fan 3 green group 138C. Leaf Vein Color: Fan 3 yellow-green group 146C. Leaf petiole color: Fan 3 yellow green group 151B.

*Pubescence*.—Upper surface of leaves: Absent. Lower surface of leaves: Absent. Margins: Absent.

*Timing of vegetative bud burst* (*early, medium, late*).—Late-early or early medium.

*Relative time of leafing versus flowering*.—When not treated with hydrogen cyanamide in mid-winter, leafing occurs after flowering.

Flowers:

*Arrangement*.—Flowers are arranged in tight cluster of flowers spiraling along branches with leaves.

*Fragrance*.—Very slight floral fragrance.

*Shape*.—Urceolate, more round with slight oval, moderate radiations.

*Flowering period*.—Mean date of 70% anthesis at Windsor, Fla. is February 21.

*Cluster*.—Tight cluster.

*Number of flowers per cluster*.—Mean of 7.2.

*Pedicel*.—Length at time of anthesis: Mean of 5.21 mm. Color at time of anthesis: Fan 3 yellow-green group N144C with Fan 2 red-purple group 64Aon the sun exposed side.

*Peduncle*.—Length at time of anthesis: Highly, variable, mean of 10.5 mm. Color at time of anthesis: Fan 3 yellow-green group N144D with Fan 2 red-purple group N57D on sun exposed side.

*Calyx*.—Surface texture: Very Smooth with slight wax. Diameter: Mean of 6.5 mm. Color (outer surface, visible at the time of anthesis without removing the corolla tube): Fan 3 green group 143A to Fan 3 yellow-green group 144D on tips of calyx lobes.

*Corolla*.—Diameter: mean of 7.9 mm. Length (from pedicel attachment point to corolla tip excluding the pedicel): Mean of 11.2 mm. Aperture diameter: Mean of 3.6 mm. Texture: Smooth with moderate radiations. Color: Fan 4 white group 155C. Anthocyanin coloration in tube: Absent.

Reproductive organs:

*Style*.—Length (top of ovary to stigma tip): Mean of 9.36 mm. Color: Fan 3 yellow-green group 149B.

*Location of tip pf stigma relative to lip of the corolla*.—Stigma tip is approximately even to 0.59 mm above the corolla lip.

*Anthers*.—Color: Fan 4 greyed-orange group 167B. Pollen: High. Pollen germination: Typically greater 90%. Color: Fan 1 yellow group 11D. Filament length: 3.4 mm. Filament width: 1.2 mm.

*Self-fruitfulness*.—Low to medium. Planting in the field configurations that promote cross fertilization with other southern highbush varieties is recommended for all southern highbush blueberry plants grown in Florida.

Fruit:

*Mean date of* 50% harvest in Citra, Fla..—April 11.

*Diameter of calyx aperture on mature berry*.—Mean of 4.0 mm.

*Size and shape of calyx lobes on mature berry*.—Very small, erect to incurving, with a moderate shallow calyx basin.

*Pedicel length on ripe berry*.—Mean of 6.2 mm.

*Detachment force for ripe berries* (*easy, medium, hard*).—Easy.

*Fruit cluster density* (*sparse, medium, dense*).—Sparse — medium.

*Number of berries per cluster*.—Mean of 3.6.

*Fruiting type*.—On one-year-old shoots and current season's shoots.

Berry:

*Cluster* (*tight, medium, loose*).—Tight.

*Weight* (*on well-pruned plants*).—Mean of 1.46 g.

*Height*.—Mean of 14.1 mm.

*Width*.—Mean of 17.3 mm.

*Shape*.—Round.

*Surface color of mature berries ripe on the plant*.—Fan 2 violet-blue group 98D.

*Intensity of fruit bloom*.—High.

*Surface color of ripe berry after polishing*.—Fan 4 black group 203C.

*Immature berry color, with bloom*.—Fan 3 yellow group 145D.

*Immature berry color, without bloom*.—Fan 3 yellow group 145C.

*Flesh color*.—Fan 4 white group NN155C.

*Surface wax*.—High and has high persistence.

*Pedicel scar*.—Small and dry. Mean of 1.23 mm.

*Firmness*.—Very firm. Mean 216 g/mm.

*Flavor*.—Sweet, with some acid hints.

*Intensity of fruit sweetness*.—Medium to high.

*Texture*.—Good texture (firm, non-mealy flesh), and no stone cells present.

*Fruit storage quality*.—Fruit is unusually firm and can be stored without shriveling, mold or loss of firmness for 4 weeks at 4° C.

Seeds:

*Color of dried seeds*.—Fan 4 greyed orange group 165A.

*Weight of* 25 *well-developed dried seeds*.—Mean of 10.6 mg.

*Length of well-developed dried seeds*.—Mean of 1.716 mm.

*Width of well-developed dried seeds*.—Mean of 0.824 mm.

Use: 'OPTIMUS' produces southern highbush blueberries suitable for machine harvest for both the fresh and processed fruit markets.

Resistance to diseases, insects, and mites: 'OPTIMUS' has grown vigorously and shows excellent bush survival in the field. It appears to be tolerant to stem blight (*Botryosphaeria* spp.) and root rot (*Phytophthora cinnamoni*), with almost no young plants dying soon after planting. Among all selections, 'OPTIMUS' is within the 3% that exhibit 95% of its plants surviving for at least 8 years when planted in a high disease field. The reaction of 'OPTIMUS' to the various fungal species that cause summer leaf spots is typical of other southern highbush varieties, and fungicide applications may be needed after harvest to reduce foliar diseases and retain leaves into the fall for maximum flower bud set. Susceptibility to typical blueberry insect and mite pathogens such as spotted wing *drosophila* (*Drosophila suzukii*), blueberry gall midge (*Dasineura oxycoccana*), blueberry flower thrips (*Frankliniella* spp), and blueberry bud mite (*Acalitus vaccini*) is similar to other southern highbush cultivars.

What is claimed is:

1. A new and distinct variety of southern highbush blueberry plant named 'OPTIMUS', as illustrated and described herein.

* * * * *